(12) United States Patent
Grancha Gamon et al.

(10) Patent No.: US 7,531,513 B2
(45) Date of Patent: May 12, 2009

(54) THERAPEUTIC PREPARATION OF VERY HIGH PURITY FVIIA AND METHOD FOR OBTAINING SAME

(75) Inventors: Salvador Grancha Gamon, Granollers (ES); Pere Ristol Debart, Sabadell (ES); Juan Ignacio Jorquera Nieto, Ametlla Del Valles (ES)

(73) Assignee: Grifols, S.A., Barcelona (ES)

( * ) Notice: Subject to any disclaimer, the term of this patent is extended or adjusted under 35 U.S.C. 154(b) by 0 days.

(21) Appl. No.: 11/672,838

(22) Filed: Feb. 8, 2007

(65) Prior Publication Data

US 2007/0197440 A1 Aug. 23, 2007

(30) Foreign Application Priority Data

Feb. 17, 2006 (ES) ................ 200600373

(51) Int. Cl.
*A61K 38/36* (2006.01)
*C07K 14/745* (2006.01)

(52) U.S. Cl. ............... 514/12; 514/2; 530/384; 424/9.1

(58) Field of Classification Search ............ 514/12, 514/2; 530/384; 424/9.1
See application file for complete search history.

(56) References Cited

U.S. PATENT DOCUMENTS

| 4,470,969 A * | 9/1984 | Pancham et al. ............ 530/381 |
| 4,479,938 A | 10/1984 | Thomas |
| 5,891,843 A * | 4/1999 | Turecek et al. .............. 514/2 |
| 2003/0232969 A1 * | 12/2003 | Lengsfeld et al. ............ 530/383 |
| 2004/0248793 A1 * | 12/2004 | Jensen et al. ................ 514/12 |
| 2006/0008792 A1 * | 1/2006 | Viswanathan et al. .......... 435/2 |
| 2007/0037966 A1 * | 2/2007 | Rasmussen et al. .......... 530/383 |

FOREIGN PATENT DOCUMENTS

| EP | 0346241 | 12/1989 |
| WO | WO-01/82943 | 11/2001 |
| WO | WO-2005/075635 | 8/2005 |

OTHER PUBLICATIONS

Tomokiyo, K. et al.: "Large-scale Production and Properties of Human Plasma-Derived Activated Factor VII Concentrate", Vox Sanguinis (2003), vol. 84, pp. 54-64.

* cited by examiner

*Primary Examiner*—Chih-Min Kam
(74) *Attorney, Agent, or Firm*—Darby & Darby, P.C.

(57) ABSTRACT

The therapeutic preparation of FVIIa having a purity of at least 1000 IU/mg of protein is characterized in that said preparation is free of proteins of non-human origin. In the method for obtaining FVII, purification starts from FrII+III, FrIII or equivalent of Cohn fractioning and comprises precipitation with PEG, chromatography and its subsequent activation.

15 Claims, No Drawings

THERAPEUTIC PREPARATION OF VERY HIGH PURITY FVIIA AND METHOD FOR OBTAINING SAME

CROSS-REFERENCE TO RELATED APPLICATIONS

This application claims priority to Spanish patent application Ser. No. 200600373 filed Feb. 17, 2006, the contents of which are hereby incorporated by reference in their entirety.

DESCRIPTION

The present invention relates to a therapeutic preparation of very high purity FVIIa and a method for obtaining same, which have notable characteristics of novelty and inventive step.

BACKGROUND

The treatment of haemorrhagic problems in haemophilia and other related disorders, such as liver disease, is carried out by means of substitution therapy with clotting factors.

The treatment of choice in haemophilia A (deficiency of clotting factor VIII) comprises the administration of said factor VIII (FVIII), both at the prophylactic level and in acute episodes. Unfortunately, one of the problems of therapy with FVIII is the appearance of FVIII-inhibiting antibodies, which reduces the efficacy of this treatment.

Other alternative treatments include the administration of concentrates of activated prothrombin complex (APCC). APCC consists of a mixture of vitamin K-dependent clotting factors (factors II, VII, IX and X) and other accompanying proteins (basically protein C and protein S). Treatment with these APCCs produces an increase in levels of the non-deficient factors, some of the factors moreover being found in their activated form, for which reason they can trigger thrombogenic phenomena in the patient, such as disseminated intravascular clotting.

The capacity of activated factor VII (FVIIa) for initiating clotting independently of the activity of factor VIII is of great therapeutic use, since it makes it possible to restore haemostasis in haemophilic patients who have developed antibodies that inhibit factor VIII and who, therefore, do not respond adequately to the substitution therapy. In comparison with other factors, FVIIa has a short biological half-life (about 4 hours), while the other factors of APCC have a longer half-life, which causes their accumulation.

Another advantage of treatment with purified FVIIa is that its action is localised by the availability of its co-factor, the tissue factor, which is released at the points of lesion (haemarthrosis, dental extractions, surgical interventions, etc.). At present, FVIIa tends to be considered as a global haemostatic agent, with a wide range of indications, such as overdose of dicumarins, liver failure, and unstoppable bleeding, among others.

In addition, in the administration of high purity FVIIa, through its high activity, the infusion of protein is minimal and other unnecessary proteins are not infused.

The preparations of FVIIa of plasmic origin have until now exhibited a relatively low FVIIa activity, in comparison with that of the present invention. Patent U.S. Pat. No. 4,479,938 for "Therapeutic composition containing factor VIIa" of BAXTER TRAVENOL LAB shows a low purity FVIIa, like patent EP0346241 for "Process for preparing a factor VIIa fraction, and its use as a medicament" of FOND NAT TRANSFUSION SANGUINE, which also shows the preparation of a low purity FVII, having an activity of between 95 and 130 IU of FVIIa/mg of protein.

The known methods of purification of FVIIa on an industrial level start from prothrombin complex or from equivalent fractions of plasmic fractioning, as shown by Patent EP0346241 and are based on methods which include selective precipitations and the use of centrifuging as a method for separating precipitates. As has been observed, in the purification processes based on precipitation, the degree of purification obtained is limited, describing moreover complex processes in which the separation of precipitates is by centrifuging, which is an industrially complex and expensive method.

Patent EP 0391974 for "Process for the purification of vitamin K-dependent blood clotting factors" of CENTRAL BLOOD LAB AUTHORITY refers basically to the purification of FIX, starting from prothrombin complex, by means of chromatography with a metal chelation column. As a by-product, proceeding from the washings from obtaining FIX, the procurement of FVII is claimed, not of FVIIa. The FVII obtained is of low purity (around one IU per mg of protein) and is characterized in that it does not contain FII, but may contain significant amounts of other vitamin K-dependent factors. By the method described, it is not possible to obtain a high purity FVIIa. Chromatography in a metal chelation column uses an activated resin with copper. In the method described in the present invention, the metal chelation chromatography uses a resin with nickel, which does not require prior activation; the washings are carried out at high conductivities, which permits stabilisation of the FVII in the column and elution does not require the presence of amino acids. This, linked also to the fact that the point of departure is a material of greater purity, makes it possible to obtain a product of high purity, which would not be achievable according to Patent EP 0391974.

Other methods for purification of plasmic FVIIa are based on the isolation and separation of FVII by immuno-affinity (with monoclonal antibodies) [Vox Sanguinis (2003) 84, 54-64]. With this method a high purity is obtained (specific activity of the order of 40,000 IU/mg of protein), but it is not possible to dismiss the presence, in the final product, of proteins of non-human origin coming from the monoclonal antibodies released by the resin used. These non-human proteins would be responsible for antigenic reactions in the patients treated.

Another aspect to be highlighted is the starting material for the process of purification of the FVIIa, which has conventionally been prothrombin complex (PTC) or an equivalent fraction. This implies that this material may be intended solely for obtaining one of the two products, either PTC or FVIIa. The possibility of purifying FVIIa starting from an alternative material, which may be a waste fraction not used in fractioning, such as the precipitate of the suspension of FrII+III, opens up the possibility of more efficient utilisation of the fractioned plasma.

SUMMARY OF THE INVENTION

By means of the present invention, a therapeutic preparation of very high purity FVIIa is obtained starting from human plasma, with at least 1000 IU/mg of protein or preferably 6000 IU/mg of protein and at a concentration of at least 12000 IU/ml. The method for obtaining this FVIIa starts from FrII+III, FrIII or equivalent of Cohn fractioning and comprises precipitation with PEG and chromatography, and the resulting product is free of proteins of non-human origin.

DESCRIPTION OF THE INVENTION

According to the present invention a therapeutic preparation of FVIIa, starting from human plasma, is described and claimed, having a purity of at least 1000 IU/mg of protein, and capable of reaching more than 6000 IU/mg of protein. This therapeutic preparation of FVIIa is free of proteins of non-human origin, and the FVIIa is present therein in a concentration of at least 12000 IU/ml.

This FVII is purified starting from fraction II+III or from fraction III or equivalents, of the fractioning of human plasma, and the purification method comprises precipitation with PEG and chromatography.

In a first stage the suspension of the starting fraction (FrII+III, Fr III or equivalent), is precipitated at a concentration of between 3 and 5% of PEG, and the resulting precipitate is dissolved and re-precipitated at a concentration of between 5 and 7% of PEG, the supernatant being recovered from this precipitation.

Starting from this supernatant, the FVII is captured by ion exchange chromatography with a resin of the Q Sepharose or Q ceramic type, and elution is carried out by change of pH.

This eluate rich in FVII is optionally purified by hydrophobic interaction chromatography with a resin of the Octyl Sepharose type. A characteristic of this procedure is that it takes place in the absence of ammonium salts.

In addition, a stage of purification of the FVII by Metal Chelation Chromatography with Ni Sepharose HP resin is carried out.

The FVII is activated in the presence of calcium.

Since this is a product of biological origin, it is advisable to include at least one, or preferably two or more stages of elimination of pathogenic agents. For its outstanding effectiveness it is convenient, for example, to include a stage of virus elimination by treatment with solvent/detergent prior to any of the chromatographic stages. This method, and the product obtained, also permit the inclusion of additional virus elimination stages, for example by nanofiltration.

In a preferred embodiment of the method described, the FVII is purified starting from FrII+III, by means of precipitation with PEG between 3.5 and 4.5% at a pH between 5 and 5.4. The precipitate obtained is re-suspended and precipitated with PEG between 5.5 and 6.5% at a pH of between 6 and 7. The adsorption of the FVII from the supernatant of this precipitation is carried out by ion exchange, with a resin of the Q-Sepharose FF type, at a pH close to neutral and eluting the FVII at a pH of between 5 and 6.

Subsequently, the FVII is optionally purified by hydrophobic interaction chromatography, adsorbing the FVII in a resin of the Octyl Sepharose FF type. This adsorption is performed at neutral pH. The purified FVII is eluted by means of a solution which contains 10 mmol/l anhydrous disodium phosphate, 10 mmol/l dihydrated trisodium citrate, 500 mmol/l NaCl at neutral pH.

The eluate, rich in FVII, is applied to a metal chelation column, with a Ni Sepharose HP resin, adsorbing the FVII at a pH between 7.5 and 8.5. This resin makes it possible to carry out washings in high conductivity conditions and also at a pH between 6 and 7. The elution of FVII with a solution which contains 10 mmol/l anhydrous disodium phosphate, 25 mmol/l NaCl, adjusted to neutral pH makes it possible to obtain a high purity FVII, with a specific activity of around 200 IU/mg of protein.

The activation of the FVII can be carried out by means of the addition of calcium, applied to any of the intermediate or final materials of the purification process, which will not vary the conditions for procurement or of the FVII described.

Likewise, one or more stages of reduction of pathogenic agents may be implemented, applied to the process described, without varying the essence of the invention.

EXAMPLE

Attached below by way of illustration is an exemplary embodiment of the present invention, divided into the consecutive stages 1 to 4.

Stage 1

Obtaining an impure fraction of FVII on precipitating the extraction of the fraction of II+III:

The initial suspension of the fraction II+III was carried out with an extraction solution of 5 mmol/l phosphate and 5% sorbitol.

Once the suspension was completed, it was maintained for 1 hour at 2-6° C. while agitating. After adjustment of the pH, PEG was added to the suspension of the fraction II+III to a final concentration of 4% (w/w). After the addition, the suspension was agitated for 30 minutes. To the previously obtained suspension, bentonite was added, agitating it afterwards for 20 minutes, from which time a rest stage of at least 4 hours commenced. After this the centrifuging process commenced for 20 minutes. Once the centrifuging process was completed, the supernatant was separated from the precipitate. The latter was dissolved in a phosphate buffer solution, the analytical evaluations of FVII being carried out, both on this material and on the initial suspension of fraction II+III. For the activity test, the COASET$^{(R)}$FVII (CHROMOGENIX) kit was used. This method is based on two steps. In the first step, the Factor X is activated to FXa by the extrinsic route (FVII-thromboplastin). The factor VII is completely activated to FVIIa during this process, therefore in this test there is no interference with the pre-activated FVII. In the second step, the Factor Xa generated hydrolyses the chromogenic substrate S-2765, releasing the chromogenic group pNA. The colour is read photometrically at 405 nm. The Factor Xa generated, and consequently the colour intensity, is proportional to the activity of Factor VII of the sample. The reconstituted PEG precipitate exhibits an activity of Factor VII of 0.86 IU/ml. These results indicate that the activity of FVII is present in the fraction II+III, and that it is recovered significantly in the precipitate, obtained on adding 4% PEG under the conditions described.

Stage 2

Obtaining and partially purifying a fraction of FVII starting from a 4% PEG precipitate, by means of the following sequential stages:

1. Precipitation with 6% PEG:

The suspension of the fraction of 4% PEG precipitate was carried out with an extraction solution (5 mmol/l phosphate, 5 mmol/l citrate and 50 mmol/l NaCl/pH 7.5 with 0.5 mol/l NaOH) at a temperature of 20-25° C. Once the re-suspension was completed it was maintained for 2 hours while agitating, afterwards being cooled to 5° C. and the pH being adjusted to 6.5. This suspension was diluted with a solution composed of 45 mmol/l phosphate, 50 mmol/l NaCl at a pH of 6.5 at 5±3° C. and PEG was added thereto until a final concentration of 6% (w/w) PEG was obtained. Finally, the supernatant of 6% PEG was clarified by means of filtration with a deep plate to separate the precipitate from the PEG. Once this process was completed, the filtered solution was analysed with respect to the activity of FVII and its protein content (estimated by optical density), obtaining a specific activity of 0.11 IU/AU. This value was calculated by dividing the activity of the FVII (IU/ml) by the approximate protein, evaluated by means of the method described in stage 1.

At this point a stage of virus inactivation by means of treatment with an organic solvent associated with a detergent is implemented. These virus inactivation reagents are afterwards separated in the following chromatographic stages.

2. Ion Exchange Chromatography:

Starting from the clarified supernatant of 6% PEG from the fraction II+III, dilution to 20% was carried out with API, adjusting the pH to 7.5 in order to reduce the conductivity. Q Sepharose FF resins (previously balanced) were then added to the previous solution, which was maintained with moderate agitation for one hour. The packing of the column (FINE LINE FF) with the suspension with resins was afterwards carried out. Once packed, the resins were washed by means of 10 mmol/l phosphate, 10 mmol/l citrate, 100 mmol/l NaCl adjusted to pH 7.5 and at a temperature of 2-8° C. When washing was completed, the elution solution Q was injected into the column. This elution was carried out with 10 mmol/l phosphate, 200 mmol/l NaCl adjusted to pH 5.5 at a temperature of 2-8° C. The eluate Q was evaluated, a specific activity of FVII of 1.16 IU/AU being obtained.

3. Hydrophobic Interaction Chromatography:

Starting from the Q Sepharose eluate, which was adjusted to 2.5 moles/l of NaCl, pH 7.0 and at a temperature of 25±3° C., the balancing of the column (Octyl Sepharose FF) was then carried out with 10 mmol/l phosphate, 10 mmol/l citrate, 2500 mmol/l NaCl at pH 7.0 and at a temperature of 25±3° C. The following step was the injection of the eluate into the column and washing with the same balancing solution (at a temperature of 25±3° C.). Elution was then carried out with 10 mmol/l phosphate, 10 mmol/l citrate, 500 mmol/l NaCl at pH 7.0 and at a temperature of 25±3° C. The octyl eluate was evaluated, obtaining results of specific activity of FVII of 3.79 IU/AU. As can be observed, the results obtained in this stage 2 reflect an increase in the specific activity over the three stages of 34 times with respect to the initial value in the clarified 6% PEG supernatant.

Stage 3 Obtaining a Pure Fraction of FVII, Starting from the Octyl Eluate by Means of MC Chromatography in Ni Sepharose HP:

Firstly, the Ni Sepharose HP column was balanced with 10 mmol/l phosphate, 1 mol/l NaCl adjusted to pH 8.0±0.05. The octyl eluate was then injected into the column. Following this, two washings were carried out, a first washing under high conductivity conditions (1 mole/l NaCl), followed by a second washing with a reduction of pH (6.5). Finally, the specific elution was carried out with a solution which comprised 10 mmole/l phosphate, 25 mmol/l NaCl, adjusted to pH 7.0. Analytical evaluations were carried out on the resulting Ni eluate, obtaining results for specific activity of 204 IU/AU, representing an increase in purity with respect to the Q eluate of some 54 times.

Stage 4 Activation of the FVII by Means of the Addition of Calcium:

In this stage the FVII was activated to FVIIa by means of the addition of calcium, starting from a Ni Sepharose eluate. For this the fraction containing the FVII was incubated at 30° C. for 20 hours in the presence of 50 mmol/l tris, 30 mmol/l NaCl and 2 mmol/l $CaCl_2$ in order to effect the auto-activation of the FVII. The analytical evaluations of these samples for the activity of FVIIa were carried out with the STACLOT$^{(R)}$ VIIa-rTF kit (DIAGNOSTICA STAGO) to the 1st International FVIIa standard. The principle of this method is based on the fact that rsTF has a specific function as co-factor of FVIIa. The rsTF in the presence of FVIIa, phospholipids and calcium produces coagulation of the plasma. In this system the clotting time observed exhibits an inverse relation to the level of FVII initially present in the plasma. The rsTF does not activate the FVII to FVIIa, therefore the FVII present in the test does not interfere in the trial. In parallel therewith, the evaluations of the activity of FVII were carried out by the method described in stage 1. The results for activity of FVII and FVIIa in the activated fraction thus obtained showed a ratio of 30.3 IU FVIIa/IU FVII.

The combination of the procedures described in the four stages makes it possible to estimate the specific activity of an activated Factor VII obtained from the Ni eluate of around 6056 IU/AU.

With the aim of eliminating viral particles or other pathogens which might be present, a final stage of nanofiltration of the solution by nanofilters of 15 nanometres pore size is implemented.

Although the invention has been explained in the preceding description, including an illustrative example, it will be understood that on the basis of what has been disclosed, experts in the field may introduce variants and alternatives included within the invention, which is limited solely by the following claims.

The invention claimed is:

1. A therapeutic preparation of factor VIIa (FVIIa) having a purity of at least 6000 IU/mg of protein, wherein the FVIIa is purified from human plasma and wherein said preparation is free of proteins of non-human origin.

2. The therapeutic preparation of FVIIa according to claim 1, wherein the FVIIa is present at a concentration of at least 12000 IU/ml.

3. The therapeutic preparation of FVIIa according to claim 1, wherein said preparation has been subjected to at least one stage of elimination of pathogenic agents, wherein the pathogenic agents include a virus or viral particle.

4. A method for obtaining a therapeutic preparation of factor VIIa (FVIIa) having a purity of at least 6000 IU/mg of protein, wherein FVII is purified from human plasma staffing from FrII+III, FrIII, or equivalent of Cohn fractioning, the method comprising precipitating FVII with PEG, and isolating FVII by chromatography followed by an independent activation step activating the separated FVII to form FVIIa, wherein said preparation is free of proteins of non-human origin.

5. The method for obtaining a therapeutic preparation of FVIIa according to claim 4, wherein the suspension of FrII+III, FrIII or equivalent of Cohn fractioning is precipitated at a concentration of between 3 and 700% of PEG.

6. The method for obtaining a therapeutic preparation of FVIIa according to claim 4, wherein FVII is captured by ion exchange chromatography.

7. The method for obtaining a therapeutic preparation of FVIIa according to claim 6, wherein ion exchange chromatography elution is carried out by change of pH.

8. The method for obtaining a therapeutic preparation of FVIIa according to claim 4, wherein FVII is purified by hydrophobic interaction chromatography.

9. The method for obtaining a therapeutic preparation of FVIIa according to claim 4, wherein the procedure is carried out in the absence of ammonium salts.

10. The method for obtaining a therapeutic preparation of FVIIa according to claim 4, wherein a stage of purification of FVII is carried out by Metal Chelation Chromatography.

11. The method for obtaining a therapeutic preparation of FVIIa according to claim 10, wherein the metal chelation chromatography is Ni-chelation chromatography.

12. The method for obtaining a therapeutic preparation of FVIIa according to claim 4, wherein the FVII is activated in the presence of calcium.

13. The method for obtaining a therapeutic preparation of FVIIa according to claim 4, wherein the method comprises at least one specific stage of virus elimination.

14. The method for obtaining a therapeutic preparation of FVIIa according to claim 13, wherein the stage of virus elimination is carried out by nanofiltration.

15. The method for obtaining a therapeutic preparation of FVIIa according to claim 13, wherein the stage of virus elimination is carried out by treatment with solvent/detergent.

* * * * *